(12) United States Patent
Jandrot-Perrus et al.

(10) Patent No.: US 9,029,095 B2
(45) Date of Patent: May 12, 2015

(54) METHOD AND KITS FOR DETERMINING PLATELET SUSCEPTIBILITY TO ACTIVATION IN A PATIENT

(75) Inventors: Martine Jandrot-Perrus, Paris (FR); Laurent Feldman, Paris (FR); Stéphane Loyau, Paris (FR)

(73) Assignees: Institut National de la Sante et de la Recherche Medicale (INSERM), Paris (FR); Universite Paris Diderot, Paris (FR)

( * ) Notice: Subject to any disclaimer, the term of this patent is extended or adjusted under 35 U.S.C. 154(b) by 0 days.

(21) Appl. No.: 13/990,887

(22) PCT Filed: Dec. 1, 2011

(86) PCT No.: PCT/EP2011/071522
§ 371 (c)(1),
(2), (4) Date: Aug. 6, 2013

(87) PCT Pub. No.: WO2012/072743
PCT Pub. Date: Jun. 7, 2012

(65) Prior Publication Data
US 2013/0310401 A1    Nov. 21, 2013

(30) Foreign Application Priority Data

Dec. 1, 2010 (EP) .................................... 10306333
Jul. 18, 2011 (EP) .................................... 11305933

(51) Int. Cl.
*G01N 33/53* (2006.01)
*G01N 33/68* (2006.01)
*G01N 33/569* (2006.01)

(52) U.S. Cl.
CPC ...... *G01N 33/6893* (2013.01); *G01N 33/56972* (2013.01); *G01N 2333/705* (2013.01); *G01N 2800/226* (2013.01)

(58) Field of Classification Search
None
See application file for complete search history.

(56) References Cited

U.S. PATENT DOCUMENTS

2007/0071744 A1 *   3/2007   Munch et al. .............. 424/133.1

FOREIGN PATENT DOCUMENTS

| EP | 1538165 A1 | 6/2005 |
| EP | 2000802 A1 | 12/2008 |
| WO | 01/00810 A1 | 1/2001 |
| WO | 2008/137753 A2 | 11/2008 |

OTHER PUBLICATIONS

Lecut et al. reference JBC 2004 vol. 279, p. 52293-52299.*
Herr, "Direct evidence of a native GPVI dimer at the platelet surface", Journal of Thrombosis and Haemostasis, Aug. 2009, pp. 1344-1346, vol. 7, No. 8.
Berlanga et al., "Glycoprotein VI oligomerization in cell lines and platelets", Journal of Thrombosis and Haemostasis, May 2007, pp. 1026-1033, vol. 5, No. 5.
Jung et al., "Glycoprotein (GP) VI dimer as a major collagen-binding site of native platelets: direct evidence obtained with dimeric GPVI-specific fabs" Journal of Thrombosis and Haemostasis, Aug. 2009, pp. 1347-1355, vol. 7, No. 8.
Malinin et al., "Monitoring platelet inhibition after clopidogrel with the VerifyNow-P2Y12(R) rapid analyzer: The VERify Thrombonis ris ASsessment (VERITAS) study", Thrombosis Research, Dec. 19, 2006, pp. 277-284, vol. 119, No. 3, Tarrytown, NY.

* cited by examiner

*Primary Examiner* — Jacob Cheu
(74) *Attorney, Agent, or Firm* — Whitham Curtis Christofferson & Cook, PC

(57) ABSTRACT

The invention relates to methods and kits for determining platelet susceptibility to activation in a patient. More particularly, the present invention relates to a method for determining platelet susceptibility to activation in a patient, comprising a step consisting of measuring the level of GPVI dimers at the platelet surface in a blood sample obtained from said patient.

19 Claims, 4 Drawing Sheets

Figure 1:
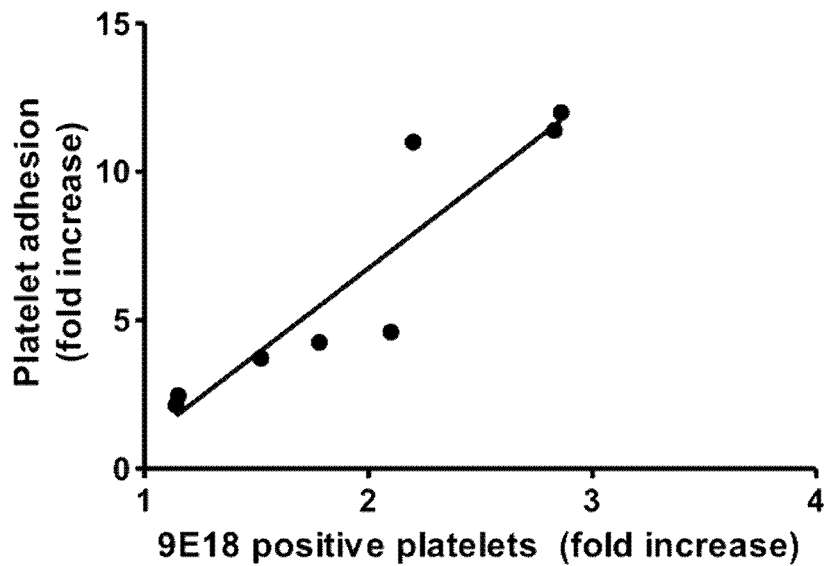

METHOD AND KITS FOR DETERMINING PLATELET SUSCEPTIBILITY TO ACTIVATION IN A PATIENT

FIELD OF THE INVENTION

The invention relates to methods and kits for determining platelet susceptibility to activation in a patient.

BACKGROUND OF THE INVENTION

Platelet adhesion at sites of vascular damage is required for normal haemostasis. Normally, platelets are prevented from activation in the blood stream by inhibitors of endothelial origin such as protacycline, nitric oxide or ectonucleotidase. However in some circumstances, dysfunctional endothelial cells loose their protective properties and promote platelet adhesion, platelet aggregation and growth of a solid thrombus on the site of the endothelial lesion.

Accordingly reliable methods for determining platelet susceptibility to activation in a patient are particularly desirable for diagnostic purposes.

Circulating platelets adhere to proteins of the subendothelial matrix exposed by an injured vessel in a process involving several receptors. Collagen fibers are highly thrombogenic and the platelet Glycoprotein (GP)VI predominantly mediates collagen-induced platelet responses.

GPVI is a platelet specific receptor of the immunoglobulin (Ig) superfamily containing two extracellular Ig domains (D1 and D2), a single transmembrane domain and a short cytoplasmic tail. GPVI shares with other receptors of the same family (e.g. FcαRI, TCR, and BCR) the particularity that the extracellular recognition (ligand-binding) domain and the intracellular signaling domain are located on separate subunits. GPVI signals through the non-covalently associated immune receptor adaptor FcRγ that presents an immunoreceptor tyrosine-based activation motif (ITAM) in its cytoplasmic domain. The receptor is assembled via a transmembrane interaction between an Asp residue in the FcRγ homodimer and an Arg residue (R273) of GPVI. Upon stimulation, the Tyr residues of the ITAM are phosphorylated in an early and obligatory event triggering the signaling cascade and the mutation of R273 prevents both GPVI association with FcRγ and collagen induced signals.

There are growing evidence that optimal binding of GPVI to collagen depends on the formation of GPVI dimers at the platelet surface. Miura and coworkers (Miura, Y., et al., *Analysis of the interaction of platelet collagen receptor glycoprotein VI (GPVI) with collagen. A dimeric form of GPVI, but not the monomeric form, shows affinity to fibrous collagen. J Biol Chem*, 2002. 277(48): p. 46197-204), using recombinant proteins, were the first to report that collagen binds to the dimeric but not to the monomeric form of GPVI and that only the former was able to attenuate collagen-induced platelet aggregation. Crystallographic data showing dimerization of GPVI ectodomains (Herr, A. B., *Direct evidence of a native GPVI dimer at the platelet surface. J Thromb Haemost*, 2009. 7(8): p. 1344-6), studies using synthetic peptides with differentially spaced GPVI binding motifs to activate the receptor in platelets (Smethurst, P. A., et al., *Structural basis for the platelet-collagen interaction: the smallest motif within collagen that recognizes and activates platelet Glycoprotein VI contains two glycine-proline-hydroxyproline triplets. J Biol Chem*, 2007. 282(2): p. 1296-304) and studies using chemical cross linking agents (Berlanga, O., et al., *Glycoprotein VI oligomerization in cell lines and platelets. J Thromb Haemost*, 2007. 5(5): p. 1026-33) have strongly reinforced the notion that GPVI functions as a dimer. However, the valence of GPVI on resting and on activated platelets respectively is still a matter of debate.

SUMMARY OF THE INVENTION

The invention relates to methods and kits for determining platelet susceptibility to activation in a patient.

More particularly, the present invention relates to a method for determining platelet susceptibility to activation in a patient, comprising a step consisting of measuring the level of GPVI dimers at the platelet surface in a blood sample obtained from said patient.

DETAILED DESCRIPTION OF THE INVENTION

The immune receptor homologue Glycoprotein VI (GPVI)/FcRγ complex is primarily responsible for platelet activation by collagen. There is growing evidence that optimal binding of GPVI to collagen depends on the assembly of GPVI dimers. The valence of GPVI on resting platelets needs to be clearly established since platelet avidity for collagen would be greater if GPVI is constitutively expressed as a dimer than as a monomer. Using a monoclonal antibody (9E18) that preferentially binds to GPVI dimers, the inventors show that GPVI is maintained in a monomeric form on human resting platelets by a cAMP/cGMP-dependent pathway. A shift towards dimerization is induced by soluble agonists and by the von Willebrand-GPIb interaction. Dimerization promotes platelet adhesion to collagen. A correlation between platelets binding of 9E18 and P-selectin exposure is observed in coronary artery diseased patients and antagonists of the ADP receptor P2Y12 limit ADP-induced dimerization of GPVI. The rapid assembly of highly competent dimers of GPVI at sites of vascular lesion represents an important new step in the sequence of events leading to platelet activation by collagen. GPVI dimers could represent a new marker to simultaneously analyse early platelet activation and platelet reactivity.

Therefore, the present invention relates to a method for determining platelet susceptibility to activation in a patient, comprising a step consisting of measuring the level of GPVI dimers at the platelet surface in a blood sample obtained from said patient.

As used herein the term "GPVI" has its general meaning in the art and refers to platelet glycoprotein VI.

The term "blood sample" means a whole blood sample obtained from the patient. The blood sample according to the invention may be a platelet rich plasma sample.

Standard methods for isolating platelets in a whole blood sample are well known in the art. For example, blood may be drawn from the patient following standard venipuncture procedure in vacutainers containing 0.109 M sodium citrate. Platelet-rich plasma (PRP) may then be obtained by centrifugation at 120 g for 15 min (room temperature) followed by pipeting of the PRP layer. Alternatively, blood may be collected on acid-citrate-dextrose anticoagulant (ACD-A) to prepare washed platelets in the presence of apyrase (25 µg/mL) and prostaglandin E1 (100 nM) as previously reported (Jandrot-Perrus, M, et al., *Cross-linking of alpha and gamma-thrombin to distinct binding sites on human platelets. Eur J Biochem*, 1988. 174(2): p. 359-67).

Standard methods for detecting the expression of a specific surface marker such as GPVI dimers at cell surface (e.g. platelet surface) are well known in the art. Typically, the step consisting of measuring the level of GPVI dimers at the platelet surface may consist in collecting a platelet population from a patient and using at least one differential binding partner directed against the GPVI dimer, wherein said platelets are bound by said binding partners to said GPVI dimers.

As used herein, the term "binding partner directed against the GPVI dimer" refers to any molecule (natural or not) that is able to bind the GPVI dimer with high affinity. Said binding partners include but are not limited to antibodies, aptamer, and peptides. It is essential according to the invention that the affinity of said binding partner for the dimeric GPVI shall be significantly higher than the affinity of said binding partner for the monomeric GPVI. Typically the affinity for the dimeric GPVI shall be 100, preferably 200 higher than the affinity for the monomeric GPVI.

The binding partners may be antibodies that may be polyclonal or monoclonal, preferably monoclonal, specifically directed against said GPVI dimer. In another embodiment, the binding partners may be a set of aptamers.

Polyclonal antibodies of the invention or a fragment thereof can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred.

Monoclonal antibodies of the invention or a fragment thereof can be prepared and isolated using any technique that provides for the production of antibody molecules by continuous cell lines in culture. Techniques for production and isolation include but are not limited to the hybridoma technique originally; the human B-cell hybridoma technique; and the EBV-hybridoma technique.

In particular embodiment, the binding partner of GPVI dimer of the invention is the 9E18.2 antibody as previously described in the international patent application WO01/00810. More particularly, the antibody is obtainable by the hybridoma cell line deposited with the ATCC as patent deposit number PTA-1749. The protelytic Fab fragment or the recombinant scFv fragment obtained from the sequence of the 9E18.2 variable domains according to published procedure (Muzard J, Bouabdelli M, Zahid M, Ollivier V, Lacapère J J, Jandrot-Perrus M, Billiald P. *Design and humanization of a murine scFv that blocks human platelet glycoprotein VI in vitro. FEBS J.* 2009 August; 276(15):4207-22) may be used.

In another embodiment, the binding partners may be aptamers. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. 1997. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consist of conformationally constrained antibody variable regions displayed by a platform protein, such as *E. coli* Thioredoxin A that are selected from combinatorial libraries by two hybrid methods.

The binding partners of the invention such as antibodies or aptamers may be labelled with a detectable molecule or substance, such as preferentially a fluorescent molecule, or a radioactive molecule or any others labels known in the art. Labels are known in the art that generally provide (either directly or indirectly) a signal.

As used herein, the term "labelled", with regard to the antibody or aptamer, is intended to encompass direct labelling of the antibody or aptamer by coupling (i.e., physically linking) a detectable substance, such as a fluorophore [e.g. fluorescein isothiocyanate (FITC) or phycoerythrin (PE) or Indocyanine (Cy5)]) or a radioactive agent to the antibody or aptamer, as well as indirect labelling of the probe or antibody by reactivity with a detectable substance. An antibody or aptamer of the invention may be labelled with a radioactive molecule by any method known in the art. For example radioactive molecules include but are not limited radioactive atom for scintigraphic studies such as I123, I124, In111, Re186, Re188.

Preferably, the antibodies against the GPVI dimer are already conjugated to a fluorophore (e.g. FITC-conjugated and/or PE-conjugated).

The aforementioned assays may involve the binding of the binding partners (i.e. antibodies or aptamers) to a solid support. The solid surface could a microtitration plate coated with the GPVI-dimer partner. After incubation of the platelet sample, platelets specifically bound to the GPVI-dimer partner may be detected with an antibody to a common platelet marker such as an antibody to CD42b such as described by Salles et al (Salles I., Broos K., Fontayne A., Szánto, Ruan C., Nurden, A T, Vanhoorelbeke K, Deckmyn H. *Development of a high-throughput ELESA assay for platelet function testing using platelet rich plasma or whole blood. Thromb Haemost.* 2010; 104:392-401). Alternatively, the solid surfaces may be beads, such as activated beads, magnetically responsive beads. Beads may be made of different materials, including but not limited to glass, plastic, polystyrene, and acrylic. In addition, the beads are preferably fluorescently labelled. In a preferred embodiment, fluorescent beads are those contained in TruCount™ tubes, available from Becton Dickinson Biosciences, (San Jose, Calif.).

According to the invention, methods of flow cytometry are preferred methods for measuring the level of GPVI dimers at the platelet surface. Said methods are well known in the art. For example, fluorescence activated cell sorting (FACS) may be therefore used. Typically, a FACS method such as described in Example here below may be used to measuring the level of GPVI dimers at the platelet surface.

In particular embodiment, the methods of the invention for detecting the expression of GPVI dimers at platelet surface (e.g. platelet surface) may also comprise use of a further binding partner directed against GPVI in all its possible forms (monomeric, dimeric or multimeric). The level of GPVI dimers could then be expressed in percentage by computing the ratio of the expression level of GPVI dimers to the expression level of total GPVI.

The binding partner directed against GPVI in all its possible forms may consist in the 3J24.2 antibody as previously described in (Lagrue-Lak-Hal A H, Debili N, Kingbury G, Lecut C, Le Couedic J P, Villeval J L, Jandrot-Perrus M, Vainchenker W. *Expression and function of the collagen receptor GPVI during megakaryocyte maturation. J Biol. Chem.* 2001 May 4; 276(18):15316-25) and the international patent application WO01/00810.

In a particular embodiment, one aliquot of the platelet rich sample may be incubated with the labelled binding partner of GPVI said dimer and another aliquot with the ligand partner of GPVI said all forms. Platelet associated fluorescence may be analysed using classically described flow cytometry methods.

The method according to the invention may further comprise a step consisting of comparing said level of GPVI dimers at the platelet surface with a reference level wherein a difference between said levels is indicative of platelet susceptibility to activation in said patient. The reference level may be expressed as a "cut-off value". For example the reference level ("cut-off value") represents a level of GPVI dimers at the platelet surface representative of a specific platelet activation state.

The methods according to the invention are particularly suitable for determining the risk of thrombosis for a patient. More particularly, the method of the present invention may be useful for predicting an acute atherothrombotic event in a patient. The method according to the present invention can thus be supplied, for prognostic purpose, to a patient, which has been diagnosed as presenting one of the following disorders:

Presence of risk factors of atherothrombosis (in particular diabetes mellitus)

Stable, symptomatic or asymptomatic (i.e., silent), myocardial ischemia

Acute coronary syndromes (with or without ST segment elevation, with or without myocardial infarction)

Patients with coronary artery disease who have been treated with one or several coronary stents (in particular drug-eluting stents, which may be at increased risk of late stent thrombosis)

Symptomatic or asymptomatic peripheral artery disease (i.e., lower limb atherothrombosis)

Abdominal aorta aneurysm

Symptomatic (i.e., stroke) or asymptomatic atherothrombosis of cerebral arteries The methods according to the present invention may also be particularly suitable for monitoring the impact of antiplatelet therapies. Typically said treatment may consist in antagonists of platelet activation and particularly of ADP receptors such as thienopyridines (e.g., clopidogrel, prasugrel) or non-thienopyridine ADP inhibitors (e.g., ticagrelor), or any newer anti-platelet agent (e.g., inhibitors of the thrombin receptor). This is supported by the observation that cAMP inhibits GPVI dimerization. ADP decreases the platelet content in cAMP via its receptor P2Y12, the target of thienopyridines. Thus, a good response to thienopyridine consists in an inhibition of the ADP-induced decrease in cAMP. This is the principle of the VASP/P2Y12 test of monitoring responsiveness to thienopyridines (e.g., clopidogrel) (Stago, American Diagnostica). Blocking P2Y12 in vitro prevented ADP-induced GPVI dimerization. An important application would thus be to monitor the efficacy of thienopyridines or other antiplatelet agents in stented patients in order to fine tune antiplatelet therapies in poor responders who are at increased risk of potentially lethal stent thrombosis.

Accordingly a further aspect of the invention relates to a method for determining the early responsiveness of a patient to a treatment with a antiplatelet agent comprising the steps consisting of i) measuring the level of GPVI dimers at the platelet surface in a blood sample obtained from said patient before said treatment and ii) measuring the level of GPVI dimers at the platelet surface in a blood sample obtained from said patient after said treatment iii) determining whether there is a change in the levels of GPVI levels from the measurement at step i) to the measurement at step ii) wherein a decrease in the level of GPVI dimers is indicative that said patient is responsive to the treatment with said antiplatelet.

In a further aspect, the invention relates to a method for determining the early responsiveness of a patient having a treatment with a antiplatelet agent comprising the steps consisting of i) providing a blood sample from said patient, preferably a platelet rich plasma sample, ii) separating said sample in two aliquots, iii) determining for said first aliquot the level of GPVI dimers at the platelet surface iv) treating the second aliquot with an activator of platelets such as ADP (adenosine diphosphate), v) determining for said second aliquot the level of GPVI dimers at the platelet surface, and vi) and comparing the levels of GPVI dimers at the platelet surface determining at step iii) and v) wherein a higher level determined at step v) than the level determined a step iii) is indicative that said patient does not respond to the antiplatelet agent.

In particular embodiment, the antiplatelet agent according to the invention is a P2Y12 inhibitor. As used herein, the term "P2Y12 inhibitor" refers to a molecule that blocks the P2Y12 protein from acting on a chemoreceptor for adenosine diphosphate (ADP). Typically P2Y12 inhibitors are exemplified by clopidogrel((+)-(S)-methyl 2-(2-chlorophenyl)-2-(6,7-dihydrothieno[3,2-c]pyridin-5(4H)-yl)acetate), ticlopidine, or prasugrel.

A further aspect of the invention related to kits for performing the methods the present invention comprising means for measuring the level of GPVI dimers at the platelet surface. The kit may include a set of binding partners as above described, in particular antibody 9E18. In a particular embodiment, the binding partners are labelled as above described. The kit may also contain other suitably packaged reagents and materials needed for the particular detection protocol, including solid-phase matrices, if applicable, and standards.

In a particular embodiment, the present invention relates to a kit suitable for determining the early responsiveness of a patient having a treatment with a antiplatelet agent comprising means for measuring the level of GPVI dimers at the platelet surface and means for activating platelet. In particular said kit may comprise the antibody 9E18. More particularly said kit may comprise an amount of ADP (adenosine diphosphate). Even more particularly said kit may comprise antibody 9E18 and an amount of ADP.

The invention will be further illustrated by the following figures and examples. However, these examples and figures should not be interpreted in any way as limiting the scope of the present invention.

FIGURES

FIG. 1: Correlation between the intensity of GPVI dimerization and the capacity of platelets to interact with collagen.

Figure 2:
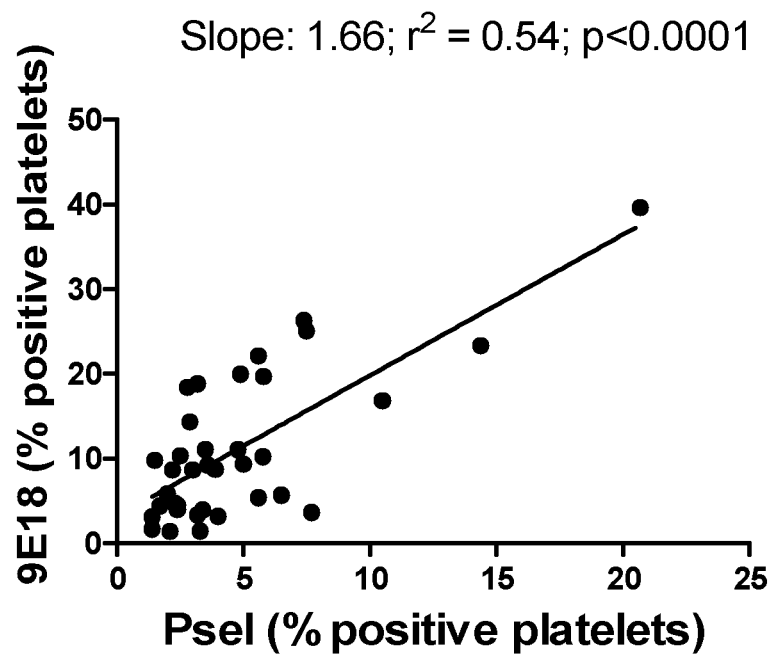

FIG. 2: Correlation of GPVI dimers and P-selectin expression in a population of patients with stable or unstable coronary artery disease hospitalized for percutaneous coronary interventions.

Figure 3:
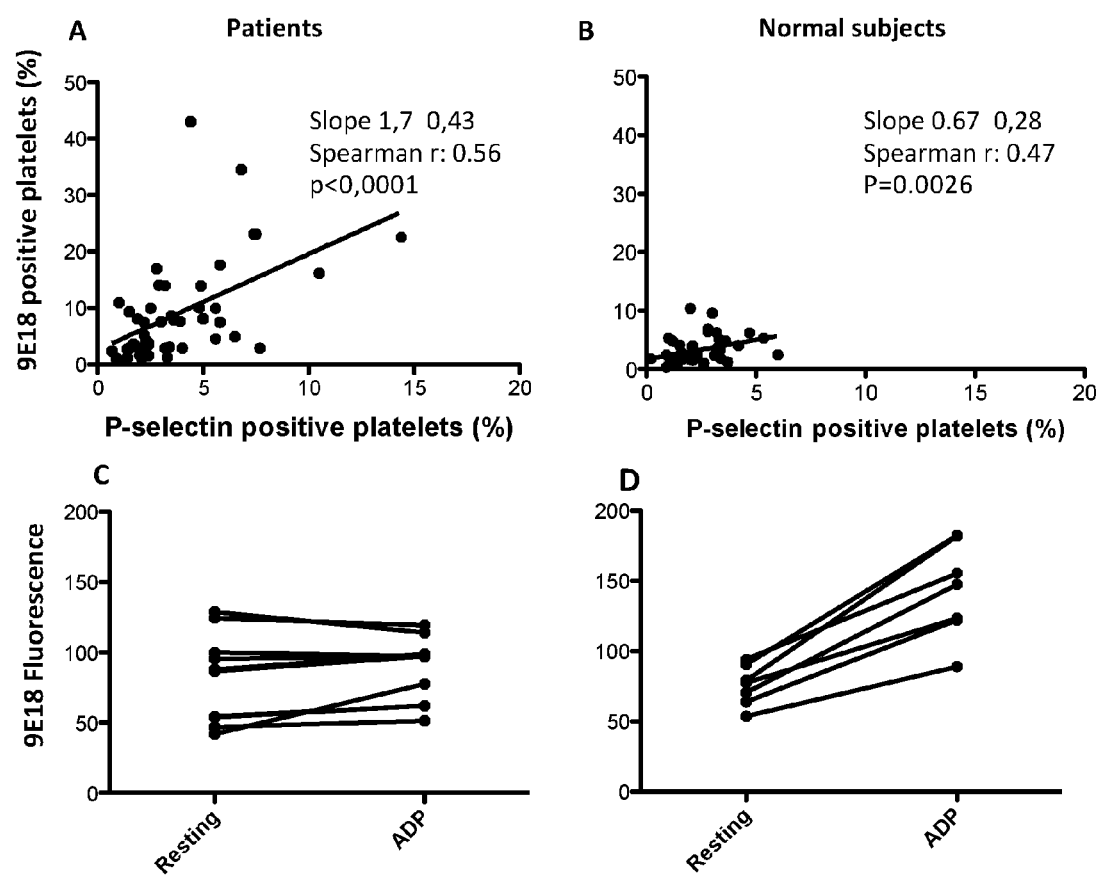

FIG. 3: 9E18 as a marker of platelet activation and reactivity: Blood samples were obtained from (A) a cohort of patients with coronary artery disease admitted for percutaneous coronary intervention (n=45) and (B) healthy volunteers (n=40). For each subject, GPVI dimerization, represented by the extent of 9E18 positive platelets, is plotted against P-selectin exposure. Blood samples were obtained from (C) patients treated by prasugel and (D) healthy volunteers. For each subject the binding of FITC-coupled 9E18 to platelets was measured by flow cytometry after incubation of the PRP with buffer or ADP (10 μM) for 20 min.

FIG. 4: 9E18 as a marker of platelet activation and reactivity A: 9E18 binding to platelets and P-selectin exposure were measured in blood samples (PRP) obtained from a cohort of patients with CAD admitted for percutaneous coronary intervention (n=45). B: ADP-induced binding of 9E18 to platelets was measured on blood samples (PRP) from normal subjects and patients with CAD treated by clopidogrel (n=26). Results are expressed as the ratio between the levels of 9E18 binding to ADP-stimulated/non-stimulated samples×100. C: ADP-induced binding to platelets of patients treated by clopidogrel was plotted against corresponding data of the VASP phosphorylation assay.

EXAMPLE 1

Material & Methods

Antibodies:

The anti-human GPVI monoclonal antibodies 3J24.2, 9012.2 and 9E18.2 were obtained as previously described. The 9012 IgG activate platelets by a mechanism involving GPVI dimerization (Lecut, C., et al., *Human platelet glycoprotein VI function is antagonized by monoclonal antibody-derived Fab fragments. J Thromb Haemost*, 2003. 1(12): p. 2653-62) whereas the 3J24 (Lagrue-Lak-Hal, A. H., et al., *Expression and function of the collagen receptor GPVI during megakaryocyte maturation. J Biol Chem*, 2001. 276(18): p. 15316-25) and 9E18 are not activating antibodies as judged from the absence of P-selectin exposure on platelets incubated with the purified IgGs. On the other hand, whereas the inhibitory effect of the 9012 Fab on collagen-induced platelet activation has been extensively documented (Lagrue-Lak-Hal, A. H., et al., *Expression and function of the collagen receptor GPVI during megakaryocyte maturation. J Biol Chem*, 2001. 276(18): p. 15316-25; Lecut, C., et al., *Human platelet glycoprotein VI function is antagonized by monoclonal antibody-derived Fab fragments. J Thromb Haemost*, 2003. 1(12): p. 2653-62; Lecut, C., et al., *Principal role of glycoprotein VI in alpha2beta1 and alphaIIbbeta3 activation during collagen-induced thrombus formation. Arterioscler Thromb Vasc Biol*, 2004. 24(9): p. 1727-33), neither the 3J24 nor the 9E18 Fab had inhibitory properties indicating that their epitope is not within the collagen binding site. HRP-coupled goat anti-mouse, Jackson ImmunoResearch, West Grove, Pa.; FITC-coupled, PE-coupled anti-P-selectin: Beckman Coulter.

Reagents:

Apyrase (grade VII), PGE1 bovine serum albumin (BSA) Sigma; thrombin receptor activating peptide (SFLLN; TRAP1) from Polypeptides (Strasbourg, France), ADP from Stago (Asnières, France); Collagen from equine tendon (Horm collagen) was from Nycomed (Munich, Germany). Convulxin was purified from the venom of *Crotallus durissus terrificus* (Francischetti, I. M., et al., *Convulxin, a potent platelet-aggregating protein from Crotalus durissus terrificus venom, specifically binds to platelets. Toxicon*, 1997. 35(8): p. 1217-28).

Recombinant soluble GPVI was obtained as the extracellular domain of human GPVI fused to the Ig domain of human immunoglobulins (GPVI-Fc that is dimeric) (Jandrot-Perrus, M., et al., Cloning, characterization, and functional studies of human and mouse glycoprotein VI: a platelet-specific collagen receptor from the immunoglobulin superfamily. Blood, 2000. 96(5): p. 1798-807) or fused to a poly-His Tag (GPVI-His that is monomeric). GPVI-Fc and GPVI-His were produced in HEK cells and affinity purified on Protein A and Ni columns respectively. Their affinity for collagen were of 1.13±0.03 µg mL-1 (5±0.2 nM) and 14.7±3.27 µg mL-1 (267±54 nM) in agreement with published data (Dumont, B., et al., *Chimeric Fc Receptors Identify Ligand Binding Regions in Human Glycoprotein VI. J Mol Biol*, 2006. 361(5): p. 877-87). Their affinity for convulxin was of 0.01 (0.65±0.0325 $10^{-10}$ M) and 0.08±0.022 µg mL-1 (1.45±0.29 $10^{-10}$ M).

Full-length recombinant GPVI was expressed in RBL 3H3 cells. Cells were transfected with pNeo containing the sequence coding for wild type or the mutant R273L GPVI which miss the capacity to complex with FcRγ. Cell surface expression of recombinant GPVI was analyzed by flow cytometry using FITC-coupled 3J24 and 9E18 IgGs.

Binding Assays Using Purified Proteins:

Experiments were conducted mainly as described (Dumont, B., et al., *Chimeric Fc Receptors Identify Ligand Binding Regions in Human Glycoprotein VI. J Mol Biol*, 2006. 361(5): p. 877-87); microtitration wells were coated with the following proteins: GPVI-Fc (0.2 µg/well) or GPVI-His (µg/well) in PBS, and saturated with BSA (Sigma, St Louis) (10 mg/mL), or purified monoclonal IgGs in PBS, containing 1 mg/mL BSA and 0.1% Tween 20, were added to the wells and incubated for the appropriate time. After washing, bound proteins were detected using appropriate secondary antibodies: HRP-coupled goat F(ab')$_2$ anti-human IgG(H+L) (Beckman Coulter, France), HRP-coupled anti His, HRP-coupled anti-mouse IgG, and O-Phenylenediamine dihydrochloride (OPD) (Sigma, St Louis Mo.). Data were analysed and graph were produced using PRISM, GraphPad, San Diego, Calif.). Affinity was determined as $K_{Dapp}=(Bmax*X^n)/[(Kd+X)^n]$.

Isolation of Platelets:

Blood was obtained from healthy volunteers who had not taken medication for 10 days after full informed consent according to the Helsinki declaration. Blood was collected in vacutainers containing 0.109 M sodium citrate; platelet-rich plasma (PRP) was obtained by centrifugation at 120 g for 15 min and platelet-poor plasma by centrifugation at 1200 g 12 min. Alternatively, blood was collected on acid-citrate-dextrose anticoagulant (ACD-A) to prepare washed platelets in the presence of apyrase (25 µg/mL) and prostaglandin E1 (100 nM) as previously reported (Jandrot-Perrus, M, et al., *Cross-linking of alpha and gamma-thrombin to distinct binding sites on human platelets. Eur J Biochem*, 1988. 174(2): p. 359-67).

Flow Cytometry:

Resting and activated platelets ($5\times10^7$ mL$^{-1}$ in whole blood or PRP or buffer) were incubated with FITC-coupled anti-GPVI or P-selectin antibodies for 20 min and, when needed fixed with 1% PFA. Samples were analyzed by flow cytometry using Epics XL.MCL (Coulter) or LSRII (Becton Dickinson Biosciences) apparatus. Platelet glycoprotein quantification was performed using the quantification kit, Platelet GP screen (Byocytex, Marseille, France).

Platelet Adhesion:

Microtiter plates were coated overnight with type I collagen (20 µg mL-1 in PBS). After blocking with BSA platelets ($10^8$ mL$^{-1}$ in reaction buffer less Mg$^{2+}$ and containing µmol L$^{-1}$ RGD peptide) were allowed to adhere for 30 min. After gentle washing, adherent platelets were quantified using p-nitophenyl phosphate as described (Lecut, C., et al., *Human platelet glycoprotein VI function is antagonized by monoclonal antibody-derived Fab fragments. J Thromb Haemost*, 2003. 1(12): p. 2653-62).

Shear-Induced Platelet Activation:

Shear induced platelet activation was performed as previously described (Ajzenberg, N., et al., *Enhanced shear-induced platelet aggregation in patients who experience subacute stent thrombosis: a case-control study. J Am Coll Cardiol*, 2005. 45(11): p. 1753-6.).

Whole Blood Flow Assay:

PPACK—anticoagulated whole blood was incubated with $DiOC_6$ (25 µM). Blood was withdrawn in collagen-coated flow chambers at a shear rate of 1,500 s$^{-1}$. Platelet adhesion to collagen was monitored continuously by fluorescence microscopy (DMIRB Leica) using a DPW camera (Olympus). After washing, platelets were labeled with 3J24 or 9E18 followed by an Alexafluor568 anti-mouse antibody.

Immunoblotting:

Washed platelets were lysed in buffer containing 20 mM Tris (pH 7.4) 3 mM EDTA, 150 mM NaCl and 2% sodium dodecyl sulfate (SDS). Proteins (10 µg) were separated by electrophoresis in SDS-polyacrylamide gels and electroblotted on a nitrocellulose membrane (Amersham Biosciences). After saturation with 5% low fat milk in PBS containing 0.1% Tween 20, the membranes were incubated with the antibodies for 2 h followed by a relevant secondary HRP-coupled IgG (Jackson ImmunoResearch, West Grove, Pa.) and bound antibodies were detected using a chemiluminescence reagent (ECL, Pierce). The loaded protein quantity was controlled using the anti-GPIb antibody SZ2 (Immunotech, France).

Patients:

Blood samples were obtained from a cohort of patients with stable or unstable coronary artery disease referred to the cardiology department of Bichat hospital for percutaneous coronary interventions (BIOCORE-2 study, Clinical Trial Registration—URL: http://clinicaltrials.gov/ct2/show/NCT01186666?term=NCT01186666&rank=1). The study complies with the Declaration of Helsinky and was approved by the institutional ethics committee. All of the patients provided written informed consent. The study was intended at finding new phenotypes of vulnerable coronary atherosclerotic plaques based on multimodal plaque imaging and circulating biomarkers. Blood was drawn on trisodium citrate the day after coronary interventions. Platelet rich plasma, a waste of the established protocol, was used for this study. Analysis was performed less than one hour after blood sampling, on PRP using FITC-coupled anti 9E18, 3J24 and P-selectin IgG.

Statistics:

Data were analyzed using PRISM, GraphPad, San Diego, Calif.). P values were calculated using a paired Student's t test (*$p<0.05$; $p<0.01$; *$p<0.005$). Correlation were determined using linear regression and Pearson two tailed analysis Results:

Antibody Binding to Monomeric and Dimeric Recombinant GPVI:

9E18 IgG bound to immobilized GPVI-His in a concentration dependent manner but with a ~30 lower affinity as compared to 3J24 (Kdapp=0.29±0.02 and 10±2 10$^{-9}$M respectively). Interestingly, when both antibodies were tested for their binding to GPVI Fc, the difference in their affinity was decreased by a factor 3. As 9E18 has been obtained from mice immunized with GPVI-Fc, we suspected the antibody could preferentially recognize dimeric GPVI and that immobilization of GPVI-His could generate a dimeric-like conformation permitting binding of 9E18. Thus, to accurately characterize the affinity of 9E18 for dimeric and monomeric GPVI respectively, we performed competition experiments. Binding of 9E18 to immobilized GPVI-Fc was fully inhibited in the presence of increasing concentrations of soluble GPVI-Fc with an IC50 of 0.055±0.026 µg·mL$^{-1}$ (0.35 10$^{-9}$M). In contrast, GPVI-His hardly prevented 9E18 binding to GPVI-Fc, with only 70% inhibition for GPVI-His up to 10 µg·mL$^{-1}$ (0.2. 10$^{-6}$M), the IC50 reaching 3.7±2.2 µg·mL$^{-1}$ (74 10$^{-9}$M). This indicates that the affinity of 9E18 for monomeric GPVI is ~200× fold lower than for dimeric GPVI. The difference in 9E18 affinity for monomeric and dimeric GPVI was further assessed by immunoblotting. Whereas 9E18 detected GPVI-Fc as 3J24.2, it hardly detected GPVI-His as compared to 3J24. Together these data indicated that 9E18 was a rather specific tool to detect dimers of GPVI.

Binding of 9E18 to Resting Platelets:

Binding of 9E18 to platelets was analyzed by flow cytometry. First, GPVI was quantified at the surface of platelets from healthy volunteers. The number of GPVI copies at the surface of washed platelets reached 5410±1330 and 1380±50 ($p<0.005$ n=3) using 3J24 and 9E18 respectively indicating that 9E18 hardly binds to GPVI on resting platelets. This data suggested that a limited number of GPVI copies could form 9E18-binding dimers on resting platelets. A low binding of 9E18 to platelets was also observed in whole blood and in PRP. Interestingly, the basal level of 9E18 binding to platelets increased progressively from whole blood to in PRP and washed platelets [2.25±0.7% (n=7), 3.1±2.4% (n=36) ands 14±1.6% positive platelets (n=20) respectively] suggesting that GPVI is mostly monomeric on circulating platelets and that the procedure used to isolate platelets induce some dimer formation. Furthermore, as compared to 3J24, 9E18 poorly detected GPVI on whole platelet lysate.

We next investigated the binding of 9E18 binding to cells expressing recombinant full length GPVI. Binding of 9E18 to WT-GPVI expressed on RBL cells was significantly lower than binding of 3J24 (18.5±4.5% vs 62±6% $p<0.001$ n=12) indicating that RBL cells express recombinant GPVI mainly as a monomer. Expression of the mutant R273L-GPVI that does not complex with FcRγ was not significantly different from expression of WT GPVI at the RBL surface. However binding of 9E18 was significantly lesser than on cells expressing WT-GPVI (5.7±1.7 vs 18.5±4.5% $p<0.03$ n=9) suggesting that GPVI association to FcRγ could favor the dimerisation process.

Binding of 9E18 to Activated Platelets:

9E18 binding to GPVI was repeated after activating platelets in different conditions. 3J34 bound equally well to washed platelets treated with TRAP (10 µM) or ADP (5 µM) as compared to resting platelets. In contrast binding of 9E18 was significantly increased on TRAP-activated platelets (from 14±1.7 to 36±7% positive platelets, n=11) and also on ADP-activated platelets but to a lesser extent (from 12.8±3.7 to 25±1.9% positive platelets, n=5). Both agonists induced surface exposure of P-selectin. A similar increase in 9E18 binding to stimulated platelets was also observed in whole blood. Binding of 9E18 to stimulated platelets was inhibited in the presence of soluble recombinant dimeric GPVI-Fc but not of soluble monomeric GPVI-His confirming that 9E18 binds to platelets on which GPVI has formed dimers.

Contrasting with the above data, the binding of 9E18 to GPVI was not increased on whole platelet lysates from activated platelets compared to resting platelets.

These data indicated 9E18 recognizes a neo-epitope exposed by GPVI dimers which formation is an activation-dependent event.

Shear-Induced GPVI Dimerization:

During platelet adhesion to vascular collagen, the initial interaction of GPIb with WF is assumed to slow down platelets and to favor GPVI interaction with collagen. GPIb-WF interaction is obtained in vitro by submitting PRP to shear. We have thus tested whether the level of GPVI dimers could be increased on shear-activated platelets. When the whole platelet population was analyzed after 5 min at 4000 s$^{-1}$, 9E18 positive platelets increased significantly from 3.6±1.6% to 7±2% ($p<0.05$ n=3). Interestingly, the number of 9E18 positive platelets was low on isolated platelets but elevated on shear-activated platelets on which 9E18 positive events reached 26±7.7%. Experiments performed with a control mouse IgG ruled out a non-specific trapping in shear-induced platelet aggregates. This data indicates that submitting platelets to an increased shear is sufficient to induce GPVI dimerization.

GPVI dimerization was further analyzed in flow conditions. Whole blood containing 9E18 or 3J24 was perfused in a collagen-coated parallel flow chamber at 1500 s$^{-1}$; Post-flux staining showed that 9E18 bound to platelet aggregates further supporting that 9E18 binding to GPVI is an activation dependent process.

GPVI Dimerization and Platelet Adhesion to Collagen:

Data from Miura et al have clearly evidenced that only the GPVI dimer has a good affinity for collagen. Preceding data also suggested a link between GPVI dimerization on platelets and platelet aggregation on immobilized collagen. We further investigated this relation by measuring in parallel 9E18 binding to stimulated platelets and GPVI-dependent platelet attachment to collagen. This was performed in conditions where the α2β1 and αIIbβ3 integrins were blocked by the absence of Mg$^{2+}$ and the presence of RGD respectively. One can observe a linear regression between binding of 9E18 and platelet adhesion to collagen ($r^2$=0.847, p=0.0012, n=8) confirming that GPVI dimerization favors GPVI-dependent platelet adhesion to collagen (FIG. 1).

Mechanisms Leading to Activation-Dependent Changes in GPVI:

In order to investigate the mechanisms leading to changes in GPVI, we searched for conditions in which 9E18 binding could be induced independently of a cell surface receptor and thus of outside-in signaling pathways. We observed that PMA significantly increased binding of 9E18 on platelets (p<0.001, n=9).

Clustering of GPVI at the platelet surface by its ligands leads to the activation of the Src family kinases (SFK) Fyn and Lyn and to phosphorylation of FcRγ on its ITAM motif. FcRγ was not phosphorylated in conditions leading to GPVI dimerization (PMA or ADP activated platelets), and the level of GPVI dimers remained unchanged on PMA-treated platelets whether they were treated with 20 μM of the Tyr-kinase inhibitor PP1 (28.4 vs 27.7%). These data indicate that GPVI dimerization and GPVI activation are different events. In contrast, the pan-kinase inhibitor staurosporine inhibited 9E18 binding to activated platelets by more than 2 fold. Previous data from our group and others have indicated that Tyr-phosphatases inhibitors prevent activation downstream of GPVI. The Tyr-phosphatase inhibitor PAO, strongly inhibited PMA-induced 9E18 binding to platelets (p<0.001, n=9). In addition, treating platelets with PMA was found to increase GPVI-dependent platelet adhesion to immobilized collagen and PAO prevented this effect. These data suggested that a Tyr-phosphatase is required for GPVI dimerization to proceed. Together, these data suggest that the formation of GPVI dimer is controlled in resting platelets by a finely tuned equilibrium between kinases and phosphatases, the nature of which remains to be determined.

Pre-incubation of platelets with activation blocking agents (apyrase and PGE1) prevented the increased 9E18 binding. Apyrase fully prevented ADP-induced binding of 9E18 and reduced TRAP-induced binding of 9E18 by 50% indicating that released ADP contributes to the assembly of GPVI dimers. The P2Y12 antagonist 2MeSAMP prevented 9E18 binding to ADP- or TRAP-stimulated platelets. In contrast, indomethacine had no effect on the binding of 9E18 induced either by ADP or by TRAP.

Interestingly, when platelets were preincubated with PGE1 alone, binding of 9E18 was lowered in the absence of agonist, dropped to basal level when platelets were stimulated by TRAP or ADP and greatly decreased when PMA was used. These data suggested that GPVI dimerization is prevented in the presence of agents increasing cAMP. This was confirmed by the inhibition of ADP-, TRAP- or PMA-induced dimerization by forskolin and IBMX and even by forskolin alone. Furthermore, the NO donor SNAP also inhibited GPVI dimerization.

GPVI Expression in Patients:

Preceding data indicated that GPVI dimerisation is an active process which favors platelet interaction with fibrillar collagen GPVI dimers could thus represent a new circulating biomarker of platelet activation in patients. To test this hypothesis, platelet 9E18 binding and P-selectin exposure were measured in PRP from 36 patients in the BIOCORE-2 study. A positive correlation was observed between 9E18 binding and P-selectin exposure (Pearson r=0.6115; p<0.0001) (FIG. 2).

Discussion:

In this study, we provide evidence that GPVI is maintained in a monomeric form on resting platelets and that GPVI dimerization is an active process that primes platelet interaction with fibrillar collagen. GPVI dimers should represent a new and sensitive marker of platelet susceptibility to activation.

Work form several groups have provided evidence that GPVI may form a dimer that has functional significance (Herr, A. B., *Direct evidence of a native GPVI dimer at the platelet surface. J Thromb Haemost*, 2009. 7(8): p. 1344-6; Berlanga, O., et al., *Glycoprotein VI oligomerization in cell lines and platelets. J Thromb Haemost*, 2007. 5(5): p. 1026-33; Arthur, J. F., et al., *Ligand binding rapidly induces disulfide-dependent dimerization of glycoprotein VI on the platelet plasma membrane. J Biol Chem*, 2007282(42): p 30434-41; Herr, A. B. and R. W. Farndale, *Structural insights into the interactions between platelet receptors and fibrillar collagen. J Biol Chem*, 2009. 284(30): p. 19781-5). The very large discrepancy between the apparent affinities of monomeric and dimeric GPVI for fibrillar collagen suggests that the dimer may recognize a specific conformational epitope on collagen. A similarly large difference in the affinities of the mAb 9E18 for monomeric and dimeric GPVI indicates that the antibody recognizes a specific conformational epitope on dimeric GPVI.

Solving the crystal structure of soluble GPVI revealed a dimeric conformation (Herr, A. B., *Direct evidence of a native GPVI dimer at the platelet surface. J Thromb Haemost*, 2009. 7(8): p. 1344-6). Furthermore, the GPVI-Fc fusion protein has demonstrated effective inhibition of thrombus formation consistent with the ability of the dimeric receptor to bind fibrillar collagen with high specificity and reasonable affinity. Since the affinities of GPVI monomers and dimers for collagen are strikingly different, the question of the stoichiometry of GPVI at the platelet surface is of importance. As compared to the major platelet receptors, the GP-IB-V-IX complex and the integrin αIIbβ3, GPVI density at the platelet surface is rather low and Kahn's group reported that signaling via GPVI in transfected cells was dependent on receptor density which could regulate dimerization (Chen, H., et al., *The platelet receptor GPVI mediates both adhesion and signaling responses to collagen in a receptor density-dependent fashion. J Biol Chem*, 2002. 277(4): p. 3011-9). However, this was not confirmed by others (Tomlinson, M G., et al., *Collagen promotes sustained GPVI signalling in platelets and cell lines. J Thromb Haemost*, 2007). Berlanga et al. obtained evidence that GPVI existed in a monomer-dimer equilibrium at the cell surface (Berlanga, O., et al., *Glycoprotein VI oligomerization in cell lines and platelets. J Thromb Haemost,* 2007. 5(5): p. 1026-33). Arthur et al. showed ligand binding triggered a very rapid disulfide cross-linking between platelet GPVI cytoplasmic domains suggesting some dimers may exist in a resting state (Arthur, J. F., et al., *Ligand binding rapidly induces disulfide-dependent dimerization of glycoprotein VI on the platelet plasma membrane. J Biol Chem,* 2007. 282(42): p 30434-41). More recently, Jung et al. provided the evidence for the existence of a specific dimer conformation of GPVI at the platelet surface (Jung, S. M., K. Tsuji, and M. Moroi, Glycoprotein (GP) VI dimer as a major collagen-binding site of native platelets: direct evidence obtained with dimeric GPVI-specific Fabs. J Thromb Haemost, 2009. 7(8): p. 1347-55.). Using phage display, they developed a mAb (204-11), which monovalent Fab (204-11 mFab) bound to dimeric but not to monomeric GPVI. However the 204-11 mFab bound to dimeric GPVI with a low affinity, 400 fold weaker than that of the 204-11 mAb. This affinity was too low to detect platelet GPVI by flow cytometry. The authors thus used a FITC-coupled secondary antibody. In these conditions they observed a slight shift to the right of the fluorescence peak that was increased in the presence of the activating 204-11 mAb suggesting that preformed dimers are present at the platelet surface. Our 9E18 antibody thus resembles the 204-11 mAb with the major differences that the 9E18 did not inhibit GPVI-binding to collagen and that it did not have the same stimulating effect than reported for the 204-11 antibody. This indicates that the 9E18 mAb is not efficient to cluster GPVI. We could thus use the FITC-coupled IgG to directly analyze the presence of the GPVI dimeric conformation at the platelet surface and to show that it has very low level on unstimulated platelets (whole blood). The difference between the data of Jung et al and the present data should rely on the method of detection, since the use of a secondary antibody in the case of 204-11 mFab should already result in some GPVI clustering. Furthermore, the fact that the proportion of dimeric GPVI increased after isolation of platelets suggested that the equilibrium between the momomeric and dimeric forms is easily shifted towards the dimer.

Importantly, we observed that stimulating platelets with a strong (TRAP) or a weak (ADP) agonist significantly increased the binding of 9E18 to platelets suggesting that stimulation brought GPVI monomers together to form dimers. This was further assessed by the fact the dimeric GPVI but not momomeric soluble GPVI inhibited 9E18 bonding to activated platelets. In the sequence of events assumed to result in stable platelet adhesion and aggregation on a platelet surface, the interaction of GPIb with collagen-bound vWF is accepted to precede and to permit GPVI binding to collagen. Using shear-induced platelet activation in PRP that is dependent on the interaction of GPIb with vWF, we provide evidence that it results in increased binding of 9E18. Additionally, we observed a significant correlation between the level of 9E18 binding and the capacity of platelets to adhere to immobilized collagen. Together, these data indicate that GPVI monomers on resting platelets are capable to form highly competent dimers and bring an important new piece to the mechanism of platelet activation by collagen.

The mechanism leading the bridging of GPVI monomers is severely controlled by cyclic AMP as indicated by the observation that PGE1 and Forskoline in the absence as in the presence of IBMX drastically reduced 9E18 binding induced by ADP, TRAP or even PMA. Elevation of cGMP by the NO-donor SNAP had the same effect. This means that in a normal vessel where platelets are bathed in PGI2 and NO produced by the endothelium, the dimerization of GPVI is prevented. However, lowering the concentration of these inhibitors allows assembly of dimers; as is observed when blood is let for more than one hour on the bench or with washed platelets.

In vivo, the formation of GPVI dimers at the platelet surface may have a priming effect by permitting more rapid interaction with collagen. Measuring the level of GPVI dimer could represent a new marker useful to quantify "primed" platelets. Precedent, studies from Gawaz's laboratory indicated that GPVI expression is an indicator for cardiovascular risk. Surface expression of GPVI was found enhanced in patients with ACS and TIA or stroke (Bigalke, B., et al., *Platelet collagen receptor glycoprotein VI as a possible novel indicator for the acute coronary syndrome. Am Heart J,* 2008. 156(1): p. 193-200; Bigalke, B., et al., *Expression of platelet glycoprotein VI is associated with transient ischemic attack and stroke. Eur J Neurol,* 2009). Using the 3J24 we also see some fluctuations in the expression of GPVI but it was not correlated to P-selectin exposure. In sharp contrast, comparing P-selectin exposure and GPVI dimer level in a population of patients hospitalized in cardiology demonstrated a good correlation for the two markers. Interestingly, while ADP activation of its receptor P2Y12 lowers the cAMP level, this effect is inhibited by the P2Y12 antagonists thienopyridines. Since GPVI dimerization is very sensitive to cAMP, this opens the possibility that measuring GPVI dimers could permit to monitor platelet susceptibility to P2Y12 antagonists.

EXAMPLE 2

Material and Methods

Antibodies:

The anti-human GPVI monoclonal antibodies 3J24, and 9E18 were obtained as previously described (Lagrue-Lak-Hal A H, Debili N Kingbury G, Lecut C, Le Couedic J P, Villeval J L, Jandrot-Perrus M, Vainchenker W. *Expression and function of the collagen receptor gpvi during megakaryocyte maturation. J Biol Chem.* 2001; 276: 15316-15325.; Lecut C, Arocas V, Ulrichts H, Elbaz A, Villeval J L, Lacapere J J, Deckmyn H, Jandrot-Perrus M. *Identification of residues within human glycoprotein vi involved in the binding to collagen: Evidence for the existence of distinct binding sites. J Biol Chem.* 2004; 279:52293-52299). They are not activating antibodies, the purified IgGs do not trigger P-selectin exposure on platelets. 3J24 and 9E18 bind to different epitopes[11]. The 9E18 IgG is able to inhibit GPVI binding to collagen (Lecut C, Arocas V, Ulrichts H, Elbaz A, Villeval J L, Lacapere J J, Deckmyn H, Jandrot-Perrus M. *Identification of residues within human glycoprotein vi involved in the binding to collagen: Evidence for the existence of distinct binding sites. J Biol Chem.* 2004; 279:52293-52299), but its Fab is far less inhibitory than the 9012 Fab on collagen-induced platelet activation (Lagrue-Lak-Hal A H, Debili N, Kingbury G, Lecut C, Le Couedic J P, Villeval J L, Jandrot-Perrus M, Vainchenker W. *Expression and function of the collagen receptor gpvi during megakaryocyte maturation. J Biol Chem.* 2001; 276:15316-15325.; Lecut C, Feeney L A, Kingsbury G, Hopkins J, Lanza F, Gachet C, Villeval J L, Jandrot-Perrus M. *Human platelet glycoprotein vi function is antagonized by monoclonal antibody-derived fab fragments. J Thromb Haemost.* 2003; 1:2653-2662; Lecut C, Schoolmeester A, Kuijpers M J, Broers J L, van Zandvoort M A, Vanhoorelbeke K, Deckmyn H, Jandrot-Perrus M, Heemskerk J W. *Principal role of glycoprotein vi in alpha2beta1* and alphaiibbeta3 activation during collagen-induced thrombus formation. *Arterioscler Thromb Vasc Biol.* 2004; 24:1727-1733). IgGs were purified and coupled to FITC according to described procedures.

Reagents:

Collagen from equine tendon (Horm collagen) was from Nycomed (Munich, Germany). Convulxin was purified from the venom of *Crotallus durissus terrificus* (Francischetti I M, Saliou B, Leduc M, Carlini C R, Hatmi M, Randon J, Faili A, Bon C. *Convulxin, a potent platelet-aggregating protein from Crotalus durissus terrificus venom, specifically binds to platelets. Toxicon.* 1997; 35:1217-1228.).

Recombinant soluble GPVI was obtained as the extracellular domain of human GPVI fused to the Ig domain of human immunoglobulins (GPVI-Fc that is dimeric) (Jandrot-Perrus M, Busfield S, Lagrue A H, Xiong X Debili N, Chickering T, Le Couedic J P, Goodearl A, Dussault B, Fraser C, Vainchenker W, Villeval J L. *Cloning, characterization, and functional studies of human and mouse glycoprotein vi: A platelet-specific collagen receptor from the immunoglobulin superfamily. Blood.* 2000; 96:1798-1807.) or fused to a poly-His Tag (GPVI-His that is monomeric). Their $K_{Dapp}$ for collagen were respectively 1.13±0.03 µg·mL$^{-1}$ (5±0.2 nM) and 14.7±3.3 µg·mL$^{-1}$ (270±54 nM) in agreement with published data (Miura Y, Takahashi T, Jung S M, Moroi M. *Analysis of the interaction of platelet collagen receptor glycoprotein vi (gpvi) with collagen. A dimeric form of gpvi, but not the monomeric form, shows affinity to fibrous collagen. J Biol. Chem.* 2002; 277:46197-46204.; Dumont B, Minullina I, Loyau S, Monteiro R C, Lacapere J J, Arocas V, Jandrot-Perrus M. *Chimeric fc receptors identify ligand binding regions in human glycoprotein vi. J Mol Biol.* 2006; 361:877-887). Monomeric GPVI was also obtained by reduction of GPVI-Fc.

Binding Assays Using Purified Proteins:

Experiments were conducted mainly as described (Dumont B, Minullina I, Loyau S, Monteiro R C, Lacapere J J, Arocas V, Jandrot-Perrus M. *Chimeric fc receptors identify ligand binding regions in human glycoprotein vi. J Mol Biol.* 2006; 361:877-887). Purified monoclonal IgGs were incubated in GPVI-coated wells in the presence of increasing amounts of soluble GPVI and detected using HRP-coupled anti-mouse IgG.

Isolation of Platelets:

Blood was obtained from healthy volunteers, who had not taken medication for 10 days, after full informed consent according to the Helsinki declaration. Platelet-rich plasma (PRP) and platelet poor plasma (PPP) were obtained by centrifugation of citrated blood. Alternatively, blood was collected on acid-citrate-dextrose anticoagulant (ACD-A) to prepare washed platelets as previously reported (Jandrot-Perrus M, Didry D, Guillin M C, Nurden A T. *Cross-linking of alpha and gamma-thrombin to distinct binding sites on human platelets. Eur J Biochem.* 1988; 174:359-367).

Platelet Adhesion and Activation:

Platelet adhesion to immobilized collagen in static conditions was measured as described (Lecut C, Feeney L A, Kingsbury G, Hopkins J, Lanza F, Gachet C, Villeval J L, Jandrot-Perrus M. *Human platelet glycoprotein vi function is antagonized by monoclonal antibody-derived fab fragments. J Thromb Haemost.* 2003; 1:2653-2662). Platelets activated by ADP, TRAP, epinephrine or PMA were analysed by flow cytometry after labeling with FITC-coupled anti-GPVI or P-selectin antibodies. Alternatively, shear-induced platelet activation was performed as previously described (Ajzenberg N, Aubry P, Huisse M G, Cachier A, El Amara W, Feldman L J, Himbert D, Baruch D, Guillin M C, Steg P G. *Enhanced shear-induced platelet aggregation in patients who experience subacute stent thrombosis: A case-control study. J Am Coll Cardiol.* 2005; 45:1753-1756). Platelet adhesion to vWF was analysed in whole blood and in flow conditions (Dumont B, Lasne D, Rothschild C, Bouabdelli M, Ollivier V, Oudin C, Ajzenberg N, Grandchamp B, Jandrot-Perrus M. *Absence of collagen-induced platelet activation caused by compound heterozygous gpvi mutations. Blood.* 2009; 114:1900-1903). Phosphorylation of vasodilatator-stimulated phosphoprotein (VASP) was measured by quantitative flow cytometry assay. Resistance to clopidogrel was defined by P2Y12 reactivity ratio>50% (Bonello L, Harhouri K, Sabatier F, Camoin-Jau L, Arnaud L, Baumstarck-Barrau K, Ait-Mokhtar O, Roubille F, Piot C, Lesavre N, Paganelli F, Dignat-George F. *Level of adenosine diphosphate receptor p2y12 blockade during percutaneous coronary intervention predicts the extent of endothelial injury, assessed by circulating endothelial cell measurement. J Am Coll Cardiol.* 2010; 56: 1024-1031).

Immunoblotting:

Proteins from whole platelets lysates were separated by electrophoresis in SDS-polyacrylamide gels and analysed by immunoblotting using anti-GPVI antibodies and secondary HRP-coupled IgG (Dumont B, Lasne D, Rothschild C, Bouabdelli M, Ollivier V, Oudin C, Ajzenberg N, Grandchamp B, Jandrot-Perrus M. *Absence of collagen-induced platelet activation caused by compound heterozygous gpvi mutations. Blood.* 2009; 114: 1900-1903).

Patients:

Blood samples were obtained from a cohort of patients with coronary artery disease (CAD) referred to the department of cardiology of Bichat hospital for percutaneous coronary intervention (BIOCORE-2 study, Clinical Trial Registration—URL: http://clinicaltrials.gov/ct2/show/NCT01186666?term=NCT01186666&rank=1). The study complies with the Declaration of Helsinky and was approved by the institutional ethics committee. All of the patients provided written informed consent. Blood was drawn on 0.109M citrate the day after percutaneous coronary intervention (PCI). PRP, a waste of the established protocol, was used for this study. Analysis was performed less than one hour after blood sampling, on PRP using FITC-coupled 9E18, 3J24 or anti-P-selectin. Alternatively, the blood was collected from patients treated by 10 mg of prasugel, in the following days of an acute coronary syndrome requiring PCI with stent implantation. Controls were healthy subjects who had taken no medication during the two previous weeks Statistics:

Data were analysed using PRISM, GraphPad (San Diego, Calif.). Box plots represent means, minimal and maximal values. P values were calculated using a paired Student's t test (*$p<0.05$; $p<0.01$; *$p<0.005$). Correlations were determined using linear regression and Spearman two-tailed analysis.

Results:

9E18 Discriminates Dimeric from Monomeric GPVI:

In preliminary experiments, 9E18 IgG were found to bind poorly to GPVI-His (monomeric GPVI) as compared to another anti-GPVI IgG, 3J24. We thus characterized the interaction of 9E18 with dimeric and monomeric GPVI in competition experiments. Binding of 9E18 to immobilized GPVI-Fc was fully inhibited in the presence of increasing concentrations of soluble GPVI-Fc with an IC50 of 0.055±0.025 µg·mL$^{-1}$ (0.36 nM). In contrast, GPVI-His was less efficient in preventing 9E18 binding to GPVI-Fc, with only 70% inhibition for GPVI-His up to 10 µg·mL$^{-1}$ (0.2 the IC50 reaching 3.7±2.2 µg·mL$^{-1}$ (Kd=78 nM). 9E18 also interacted poorly with the reduced form of GPVI-Fc. The affinity of 9E18 for monomeric GPVI is thus ~200× fold lower than for dimeric GPVI. Immunoblotting confirmed the poor capacity of 9E18 to detect GPVI-His or reduced GPVI-Fc. 9E18 allows thus to discriminate GPVI dimers from momomers.

Binding of 9E18 to Resting Platelets:

By flow cytometry, a very low level of 9E18 binding to platelets was observed in whole blood. Interestingly, the basal level of 9E18 binding to platelets increased progressively from whole blood to PRP and washed platelets [2.25±0.7% (n=7), 3.1±2.4% (n=36) and 14±1.6% (n=20) positive platelets respectively]. These data indicate that GPVI is mostly monomeric on circulating platelets; a very limited number of GPVI copies can form dimers on resting platelets but platelet isolation favors the assembly of supplemental dimers. Furthermore, Furthermore, GPVI was poorly detected using 9E18 on a whole platelet lysate.

Binding of 9E18 to Activated Platelets:

3J34 bound equally well to washed platelets treated with TRAP or ADP as to resting platelets (80±3% and 91±4% vs 85.5±3%). In contrast, binding of 9E18 significantly increased from 14±1.6% to 36.2±7% on TRAP-activated washed platelets and, to a lesser extent (25±5%) on ADP-activated platelets. Both agonists also induced surface exposure of P-selectin. A similar increase in 9E18 binding to stimulated platelets was observed in whole blood. Epinephrine (0.5 µM) increased the binding of 9E18 to platelets by a factor 1.5 and this effect was additive with this of ADP. The IV.3 monoclonal antibody did not prevent 9E18 binding to activated platelets, ruling out a non-specific binding of 9E18 to FcγRIIA. Furthermore, binding of 9E18 to stimulated platelets was only and dose-dependently inhibited by GPVI dimers, and not by monomers. In addition, even after platelet activation 9E18 still poorly detected the 58 kDa band, corresponding to monomeric GPVI.

Together, these data indicate that 9E18 recognizes an epitope exposed by GPVI dimers whose formation is an activation-dependent event.

Shear-Induced Binding of the 9E18 Antibody:

The initial interaction of GPIb with vWF being assumed to slow down platelets and to favor GPVI interaction with collagen, it was triggered in vitro by high shear stress. 9E18 binding increased from 3.6±1.6% after 5 min at 0 s$^{-1}$ to 7±2% at 4000 s$^{-1}$ (p<0.05 n=3). Interestingly, while the number of 9E18 positive events was low in the gate corresponding to isolated platelets (2.7±0.4%), it was increased up to 26±7.7% in the gate focused on shear-induced aggregates. Experiments performed with a control mouse IgG ruled out any non-specific trapping in shear-induced platelet aggregates. When experiments were repeated on washed platelets, the addition of vWF induced a parallel increase in shear-induced platelet aggregation and in the level of 9E18 binding. P-selectin exposure was also observed on platelet aggregates. When whole blood was perfused in vWF-coated flow chambers at 1500 s$^{-1}$, post-flux staining by 9E18 was clearly positive on platelet aggregates and on platelets showing signs of activation, further supporting that platelet interaction with vWF is able to trigger GPVI dimerization.

Platelet Adhesion to Collagen:

To investigate whether binding of 9E18 was related to the capacity of platelets to interact with collagen, 9E18 binding and GPVI-specific platelet attachment to collagen were measured simultaneously, α2β1 and αIIbβ3 integrins being blocked by the absence of Mg$^{2+}$ and the addition of RGD. A significant linear correlation was observed between binding of 9E18 and adhesion to collagen (r$^2$=0.87, p=0.0002, n=9) indicating that the conformation of GPVI recognized by 9E18 is favorable for GPVI-dependent platelet adhesion to collagen.

Figure 4A:
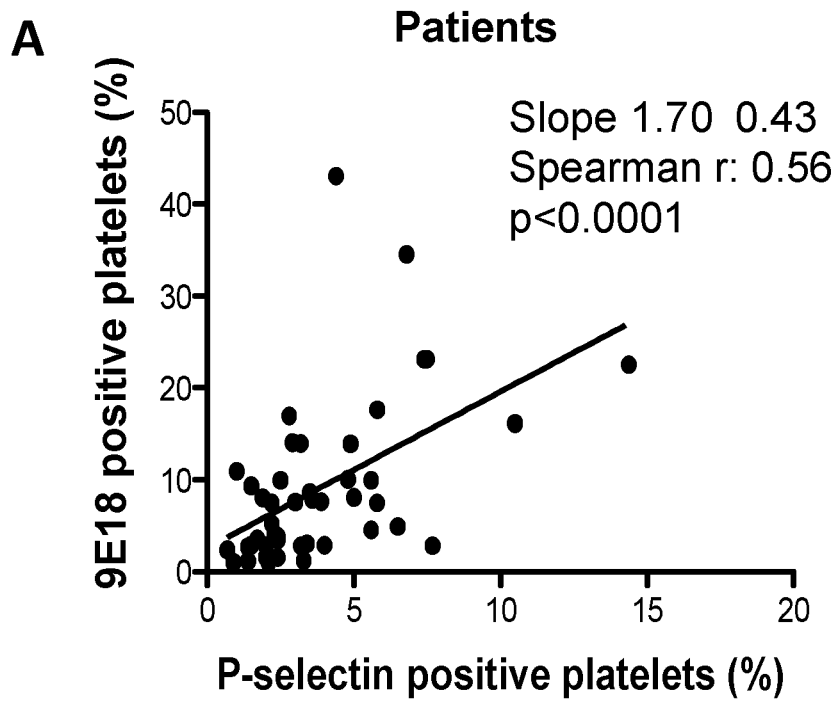

Mechanisms Leading to Activation-Dependent Changes in GPVI:

As binding of 9E18 to platelet was induced by receptor activation, we examined whether it could be induced independently of a cell surface receptor and found that PMA increased the level of 9E18 binding to platelets up to 31.5±4% (p<0.001).

cAMP is established as limiting platelet activation. Adenylate cyclase is inhibited by ADP-activation of its receptor P2Y12 and activated by prostacycline. While ADP increased the binding of 9E18, PGE1 reduced it on washed resting platelets, as well as on TRAP-, ADP- or PMA-activated platelets (FIG. 4A). Forskolin and IBMX induce a receptor-independent elevation of cAMP via the direct activation of adenylate cyclase and the inhibition of phosphodiesterase respectively. Forskolin plus IBMX (FIG. 4A) and even forskolin alone (data not shown) inhibited 9E18 binding to resting, or ADP-, TRAP- or PMA-activated platelets.

NO donors which increase intraplatelet cGMP concentration are also inhibitors of platelet activation; the NO donor SNAP inhibited 9E18 binding to resting as to TRAP-ADP-od PMA activated platelets (FIG. 4A).

Figure 4B:
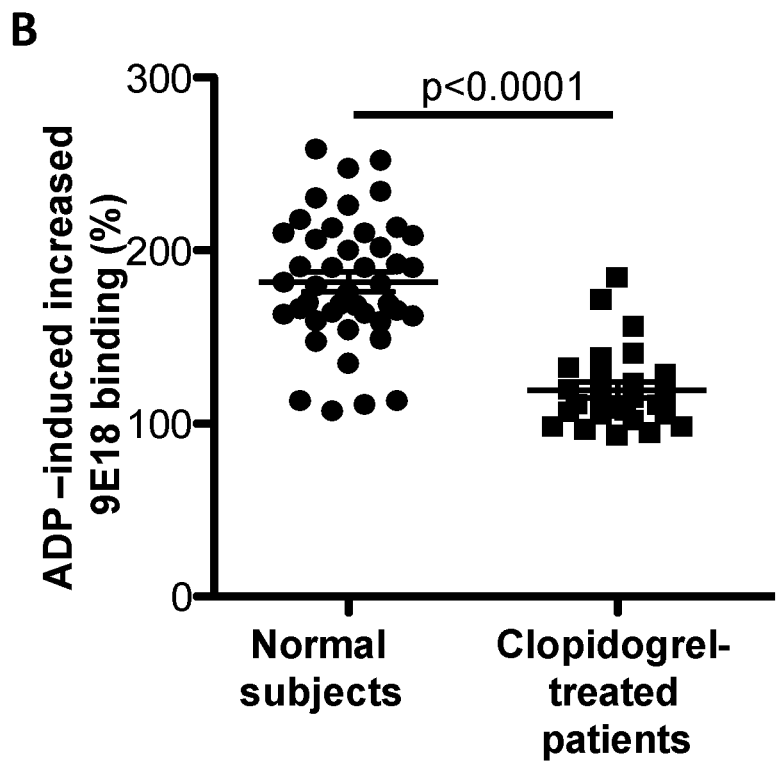
Figure 4C:
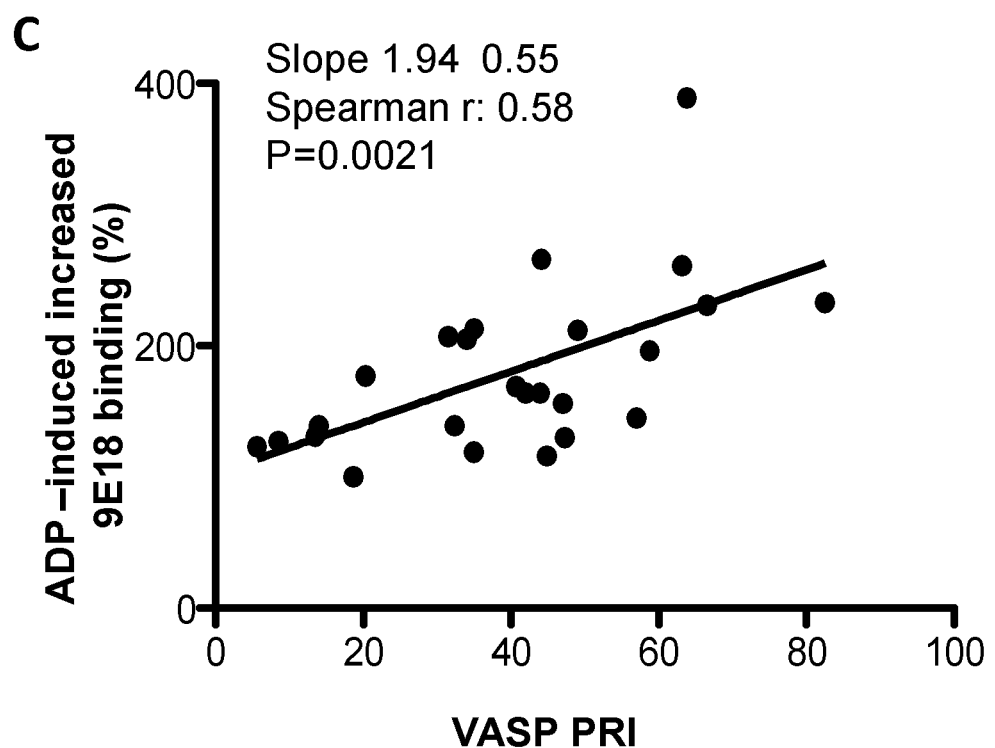

The role of endogenous platelet agonists in 9E18 binding to platelets was analyzed. Indomethacin had no effect on the level of 9E18 binding to stimulated platelets ruling out a role of TXA2. In contrast, apyrase inhibited both ADP- and TRAP-induced binding of 9E18 by 85 and 75% respectively indicating that released ADP contributes to GPVI changes. The P2Y12 antagonist, 2MeSAMP, also inhibited 9E18 binding to ADP- or TRAP-stimulated platelets (data not shown). Phenylarsine oxide, a reagent that binds to vicinal sulfhydryls previously reported to inhibit GPVI-dependant platelet activation[19, 20] is commonly used at low concentration as an inhibitor of phosphotyrosine phosphatases. It fully prevented PMA-induced binding of 9E18 to platelets and GPVI-dependent platelet adhesion to immobilized collagen but was without effect on P-selectin exposure (FIG. 4B-C)

In contrast, PMA-induced binding of 9E18 remained unchanged in the presence 20 µM of the Tyr-kinase inhibitor PP1 (28.4 vs 27.7%). FcRγ was not phosphorylated in conditions leading to GPVI dimerization (PMA- or ADP-activated platelets), indicating that binding of 9E18 to platelets occurs independently of GPVI-downstream signals.

Binding of 9E18 is a Potential New Marker of Platelet Activation and Efficacy of Prasugrel:

Since binding of 9E18 is the consequence of an active GPVI modification which favors platelet interaction with fibrillar collagen, it could represent a new circulating biomarker of platelet activation in patients. To test this hypothesis, 9E18 binding and P-selectin exposure were measured in PRP from CAD patients (n=45) participating in the BIOCORE-2 study. A positive correlation was observed between 9E18 binding and P-selectin exposure (Spearman r=0.568; p<0.0001) (FIG. 3 A,B). A positive, but less significant, correlation was also observed between P-selectin and 9E18 positive platelets in a population of healthy volunteers (n=40) (Spearman r=0.47; p=0.0026).

On the other hand, ADP induced an increased binding of 9E18 to platelets of all controls, but not to platelets of 9 patients treated by prasugrel who were considered as good responders with the VASP phosphorylation test. Interestingly, in one case, both 9E18 binding and VASP phosphorylation remained increased in response to ADP, suggesting a low response to prasugrel (FIG. 3C,D).

Discussion:

In this study, using the mAb 9E18 as a specific tracer of dimeric GPVI we demonstrate that GPVI is maintained in a monomeric form on resting platelets and that GPVI dimerization is an active process, controlled by cAMP, and which primes platelet interaction with fibrillar collagen. Consequently, GPVI dimers could represent a new, sensitive and early marker of platelet activation and of platelet responsiveness.

Several groups have reported that GPVI may form a dimer that has functional significance (Berlanga O, Bori-Sanz T, James J R, Frampton J, Davis S J, Tomlinson M G, Watson S P. *Glycoprotein vi oligomerization in cell lines and platelets. J Thromb Haemost.* 2007; 5:1026-1033; Jung S M, Tsuji K, Moroi M. *Glycoprotein (gp) vi dimer as a major collagen-binding site of native platelets: Direct evidence obtained with dimeric gpvi-specific fabs. J Thromb Haemost.* 2009; 7:1347-1355; Herr A B. *Direct evidence of a native gpvi dimer at the platelet surface. J Thromb Haemost.* 2009; 7:1344-1346; Arthur J F, Shen Y, Kahn M L, Berndt M C, Andrews R K; Gardiner E E. *Ligand binding rapidly induces disulfide-dependent dimerization of glycoprotein vi on the platelet plasma membrane. J Biol Chem.* 2007; 282:30434-30441). The very large discrepancy between the apparent affinities of monomeric and dimeric GPVI for fibrillar collagen suggests that the GPVI dimer acquires a specific conformation suitable for binding to collagen. A similarly large difference in the affinities of the mAb 9E18 for monomeric and dimeric GPVI indicates that the antibody recognizes a specific conformational epitope on dimeric GPVI. The observation that 9E18 specifically binds to activated platelets and that binding of 9E18 is exclusively inhibited by soluble GPVI dimers, suggests that a dimeric-specific epitope could be exposed by platelet GPVI X-Ray crystallography of soluble GPVI revealed a dimeric conformation. Furthermore, the GPVI-Fc fusion protein has demonstrated effective inhibition of thrombus formation, consistent with its ability to bind fibrillar collagen with high specificity and reasonable affinity. Thus, the initial interaction of platelets with collagen would be favoured by the existence of preformed dimers of GPVI at the platelet surface. Actually, Kahn's group reported that signaling via GPVI in transfected cells was dependent on receptor density which could regulate dimerization (Chen H, Locke D, Liu Y, Liu C, Kahn M L. *The platelet receptor gpvi mediates both adhesion and signaling responses to collagen in a receptor density-dependent fashion. J Biol Chem.* 2002; 277:3011-3019.), but this was not confirmed by others (Tomlinson M G, Calaminus S D, Berlanga O, Auger J M, Bori-Sanz T, Meyaard L, Watson S P. *Collagen promotes sustained glycoprotein vi signaling in platelets and cell lines. J Thromb Haemost.* 2007; 5:2274-2283). GPVI has been proposed to be in a monomer-dimer equilibrium at the platelet surface (Berlanga O, Bori-Sanz T, James J R, Frampton J, Davis S J, Tomlinson M G, Watson S P. *Glycoprotein vi oligomerization in cell lines and platelets. J Thromb Haemost.* 2007; 5:1026-1033) and ligand binding triggered a very rapid disulfide cross-linking of the GPVI cytoplasmic domains, suggesting that some dimers may exist in the resting state (Arthur J F, Shen Y, Kahn M L, Berndt M C, Andrews R K, Gardiner E E. *Ligand binding rapidly induces disulfide-dependent dimerization of glycoprotein vi on the platelet plasma membrane. J Biol Chem.* 2007; 282: 30434-30441). More recently, Jung et al. provided evidence for the existence of a specific dimer conformation of GPVI at the platelet surface (Jung S M, Tsuji K, Moroi M. *Glycoprotein (gp) vi dimer as a major collagen-binding site of native platelets: Direct evidence obtained with dimeric gpvi-specific fabs. J Thromb Haemost.* 2009; 7:1347-1355). The mAb (204-11) is activating platelets; its monovalent Fab (204-11 mFab) did not bind to GPVI monomers but bound to dimers with a very low affinity. Using this mFab the authors identified preformed dimers at the platelet surface. However, they used of a secondary antibody that may by itself cause some GPVI dimerization. In contrast, FITC-9E18 IgG could be used directly to detect GPVI dimers on platelets without clustering the receptor. This allowed us to show that, actually, GPVI dimers are scarce on unstimulated platelets, particularly in whole blood. Furthermore, the fact that the binding of 9E18, and thereby the proportion of dimeric GPVI, increased after isolation of platelets suggests that the equilibrium between the monomeric and dimeric forms is easily shifted towards the latter.

Importantly, we observed that stimulating platelets with a weak (ADP) or a strong (TRAP) soluble agonist, significantly increased the binding of 9E18 to platelets thus suggesting that platelet stimulation brought GPVI monomers together to form dimers. In the sequence of events assumed to result in stable platelet adhesion and aggregation, the interaction of GPIb with collagen-bound vWF is thought to precede GPVI binding to collagen. We observed that shear-induced platelet activation and flow-induced platelet adhesion to vWF, both responses dependent on GPIb interaction with vWF, actually triggered GPVI dimerization. We thus demonstrate for the first time that the vWF/GPIb axis has a priming effect on GPVI, resulting in a direct enhancement of GPVI interaction with collagen. The rapid assembly of highly competent dimers of GPVI at sites of vascular lesion represents an important new step in the sequence of events leading to platelet activation by collagen.

The mechanism leading to GPVI dimerization is clearly distinct from the signaling cascade downstream to GPVI: it did require neither FcRγ phosphorylation nor the activation of downstream Tyr-kinases. Since the assembly of a GPVI dimer is not sufficient to trigger downstream signalling, clusters at least two GPVI-dimers appear to be the minimal signaling unit (Herr A B. *Direct evidence of a native gpvi dimer at the platelet surface. J Thromb Haemost.* 2009; 7: 1344-1346; Sigalov A B. *Novel mechanistic concept of platelet inhibition. Expert Opin Ther Targets.* 2008; 12:677-692). Nevertheless, the shift from monomeric to dimeric GPVI requires the activity of kinases and phosphatases. Activation of GPVI dimerization by PMA and inhibition by staurosporine suggest the involvement of a Ser/Thr-kinase which remains to be identified, but a Tyr-kinase-dependent pathway cannot completely excluded even if PP1 had no effect. The strong inhibition of PMA-induced GPVI dimerization by PAO is consistent with our previous observation that PAO blocked collagen-induced platelet activation and further in favor of a Tyr-phosphatase critically involved in the dimerization of GPVI upstream to its activation (Lagrue A H, Francischetti I M, Guimaraes J A, Jandrot-Perrus M. *Phosphatidylinositol 3'-kinase and tyrosine phosphatase activation positively modulate convulxin-induced platelet activation. Comparison with collagen. FEBS Lett.* 1999; 448:95-100.). Recent studies have provided evidence that the Src family kinase Lyn, constitutively bound to the Pro-rich motif of the GPVI cytoplasmic domain, is in an activated state (Schmaier A A, Zou Z, Kazlauskas A, Emert-Sedlak L, Fong K P, Neeves K B, Maloney S F, Diamond S L, Kunapuli S P, Ware J, Brass L F, Smithgall T E, Saksela K, Kahn M L. *Molecular priming of lyn by gpvi enables an immune receptor to adopt a hemostatic role. Proc Natl Acad Sci USA.* 2009;

106:21167-21172) and that CD148, a phosphatase important in the initiation of the GPVI-signaling cascade, maintains a pool of active SFKs (Senis Y A, Tomlinson M G, Ellison S, Mazharian A, Lim J, Zhao Y, Kornerup K N, Auger J M, Thomas S G, Dhanjal T, Kalia N, Zhu J W, Weiss A, Watson SP. *The tyrosine phosphatase cd148 is an essential positive regulator of platelet activation and thrombosis. Blood.* 2009; 113:4942-4954). Whether this molecular priming mechanism is linked to GPVI dimerization remains to be determined.

Importantly, PGE1 inhibited 9E18 binding to ADP-, TRAP- or PMA-activated platelets, demonstrating that cAMP is a critical regulator of GPVI dimerisation. This was confirmed by the observation that forskolin similarly blocked the assembly of GPVI dimers. Furthermore SNAP, which increases the cGMP concentration, also inhibited GPVI dimerization.

Our findings provide new insight into the molecular regulation of platelet interaction with the sub-endothelial collagen matrix. In healthy vessels, GPVI is maintained in a monomeric form on circulating platelets by the continual production of prostacyclin and NO by endothelial cells. However, a shift towards GPVI dimerization could be induced by endothelial dysfunction or high shear rate, and may have a priming effect, permitting a more rapid interaction of platelets with collagen.

Measuring the level of GPVI dimers could therefore represent a new marker for the detection of "primed" platelets. Surface expression of GPVI has been proposed to represent an indicator for cardiovascular risk since it was reported as enhanced in patients with acute coronary syndrome, transient ischemic attack or stroke (Bigalke B, Geisler T, Stellos K, Langer H, Daub K, Kremmer E, Seizer P, May A E, Lindemann S, Gawaz M. *Platelet collagen receptor glycoprotein vi as a possible novel indicator for the acute coronary syndrome. Am Heart J.* 2008; 156:193-200; Bigalke B, Stellos K, Geisler T, Kremmer E, Seizer P, May A E, Lindemann S, Melms A, Luft A, Gawaz M. *Expression of platelet glycoprotein vi is associated with transient ischemic attack and stroke. Eur J Neurol.* 2010; 17:111-117). The present study, comparing P-selectin exposure and GPVI dimer levels in patients suffering from CAD demonstrates a good correlation between the two markers.

On the other hand, cAMP inhibits GPVI dimerization whereas antagonists of the ADP receptor P2Y12 prevent the lowering effect of ADP on cAMP (Defreyn G, Gachet C, Savi P, Driot F, Cazenave J P, Maffrand J P. *Ticlopidine and clopidogrel (sr 25990c) selectively neutralize adp inhibition of pge1-activated platelet adenylate cyclase in rats and rabbits. Thromb Haemost.* 1991; 65:186-190). The measure of ADP-induced binding of 9E18 to platelets could thus represent a new marker estimating simulatelously the biological and the functional efficiency of P2Y12 antagonists. This is supported by the observations that ADP-induced GPVI dimerization is blocked (i) in vitro by the P2Y12 antagonist 2MeSAMP and (ii) ex vivo, on platelets from patients treated by a potent thienopyridine, prasugrel.

In conclusion, GPVI dimerisation measured with 9E18 is a potentially new tracer offering the opportunity to monitor both the activation state of platelets and their reactivity to P2Y12 antagonists. GPVI dimerization could be considered as an early biomarker of platelet activation compared to P-selectin, according to the sequence of events leading to platelet activation. Numerous platelet function tests are proposed to determine good responders to P2Y12 antagonists however there is no consensus regarding the most appropriate method. GPVI dimerization could be of great interest since it integrates the initial activation state and the degree of platelet inhibition. It represents a mechanistic marker of thiénopyridine as the VASP phosphorylation test combined with the advantage of being also a functional marker.

EXAMPLE 3

Binding of 9E18 is a Potential New Marker of Platelet Activation and Efficacy of Clopidogrel Since binding of 9E18 is the consequence of an active GPVI modification which favors platelet interaction with fibrillar collagen, it could represent a new circulating biomarker of platelet activation in patients. To test this hypothesis, 9E18 binding and P-selectin exposure were measured in PRP from CAD patients (n=45) participating in the BIOCORE-2 study. All patients were under dual antiplatelet therapy, aspirin (75 to 160 mg/day) and clopidogrel (75 mg/day). A positive correlation was observed between basal 9E18 binding and P-selectin exposure (Spearman r=0.568; p<0.0001) (FIG. 4A). We hypothesized that antagonists of P2Y12 could inhibit ADP-induced 9E18 binding to platelets. To test this hypothesis, 9E18 binding to platelets was measured before and after PRP incubation with ADP in normal subjects, and patients treated by clopidogrel (75 mg) (FIG. 4B). A highly significant reduction of the response was observed in clopidogrel-treated patients. A good correlation was found between ADP-induced 9E18 binding and the VASP phosphorylation test, which is one of the biological markers of P2Y12 antagonists (FIG. 4C).

REFERENCES

Throughout this application, various references describe the state of the art to which this invention pertains. The disclosures of these references are hereby incorporated by reference into the present disclosure.

The invention claimed is:

1. A method for determining platelet susceptibility to activation in a human patient, comprising the steps of
measuring the level of Glycoprotein VI (GPVI) dimers at the platelet surface in a blood sample obtained from said patient by contacting the blood sample with a binding partner that binds to the GPVI dimer with high affinity wherein said binding partner is an antibody directed against said GPVI dimer; and
detecting platelets bound by said binding partner; and
comparing said level of GPVI dimers at the platelet surface with a reference level representative of the level of GPVI dimers measured on resting platelets wherein when the level of said level of GPVI dimers at the platelet surface is higher than the reference level it is concluded that the patient's platelets are susceptible to activation.

2. The method according to claim 1 wherein said antibody is the 9E18.2 antibody.

3. The method according to claim 1 wherein the level of GPVI dimers is expressed as a percentage by computing a ratio of an expression level of GPVI dimers to an expression level of total GPVI.

4. The method according to claim 1 wherein the level of GPVI dimers at the platelet surface is determined by a flow cytometry method.

5. A method for determining the early responsiveness of a human patient to a treatment with an antiplatelet agent comprising the steps of i) measuring the level of GPVI dimers at the platelet surface in a blood sample obtained from said patient before said treatment,
ii) administering said treatment to said patient,
iii) measuring the level of GPVI dimers at the platelet surface in a blood sample obtained from said patient after said treatment, and
iv) determining whether there is a change in the levels of GPVI from the measurement at step i) to the measurement at step iii) wherein a decrease in the level of GPVI dimers is indicative that said patient is responsive to the treatment with said antiplatelet agent.

6. A method for determining the early responsiveness of a human patient having a treatment with an antiplatelet agent comprising the steps of
i) providing a blood sample from said patient,
ii) separating said sample in two aliquots,
iii) determining for said first aliquot the level of GPVI dimers at the platelet surface
iv) treating the second aliquot with an activator of platelets,
v) determining for said second aliquot the level of GPVI dimers at the platelet surface, and
vi) and comparing the levels of GPVI dimers at the platelet surface determining at step iii) and v) wherein a higher level determined at step v) than the level determined a step iii) is indicative that said patient does not respond to the antiplatelet agent.

7. The method according to claim 5 wherein said antiplatelet agent is a P2Y12 inhibitor.

8. The method according to claim 6 wherein said P2Y12 inhibitor is selected from the group consisting of clopidogrel ((+)-(S)-methyl 2-(2-chlorophenyl)-2-(6,7-dihydrothieno[3,2-c]pyridin-5(4H)-yl)acetate), ticlopidine, and prasugrel.

9. A method for preventing thrombosis in a human patient using an antiplatelet agent comprising the steps of
a) determining early responsiveness of the patient to treatment using said antiplatelet agent by
i) measuring a level of GPVI dimers at the platelet surface in a blood sample obtained from said patient before said treatment,
ii) administering said antiplatelet agent to said patient,
iii) measuring the level of GPVI dimers at the platelet surface in a blood sample obtained from said patient after said step of administering, and
iv) determining whether there is a change in the levels of GPVI from the measurement at step i) to the measurement at step iii), wherein a decrease in the level of GPVI dimers is indicative that said patient is responsive to the treatment with said antiplatelet agent, and
b) continuing to administer said antiplatelet agent to said patient if the patient is considered as responsive at step iv), thereby preventing thrombosis in said patient.

10. The method according to claim 6 wherein said blood sample is a platelet rich plasma sample.

11. The method according to claim 6 wherein said antiplatelet agent is a P2Y12 inhibitor.

12. The method according to claim 11 wherein said P2Y12 inhibitor is selected from the group consisting of clopidogrel ((+)-(S)-methyl 2-(2-chlorophenyl)-2-(6,7-dihydrothieno[3,2-c]pyridin-5(4H)-yl)acetate), ticlopidine, and prasugrel.

13. The method of claim 9, further comprising a step of diagnosing said patient as having a disorder selected from the group consisting of: at risk for atherothrombosis, stable myocardial ischemia, symptomatic myocardial ischemia, asymptomatic myocardial ischemia, an acute coronary syndrome, coronary artery disease that has been treated with one or several coronary stents, symptomatic peripheral artery disease, asymptomatic peripheral artery, abdominal aorta aneurysm, symptomatic atherothrombosis of cerebral arteries and asymptomatic atherothrombosis of cerebral arteries.

14. A method for preventing thrombosis using an antiplatelet agent, comprising the steps of
a) determining the early responsiveness of a human patient to a treatment using said antiplatelet agent by:
i) providing a blood sample from said patient,
ii) separating said sample in two aliquots,
iii) determining for said first aliquot the level of GPVI dimers at the platelet surface,
iv) treating the second aliquot with a activator of platelets,
v) determining for said second aliquot the level of GPVI dimers at the platelet surface, and
vi) comparing the levels of GPVI dimers at the platelet surface determined at steps iii) and v) wherein a lower level determined at step v) than the level determined a step iii) is indicative that said patient responds to the antiplatelet agent; and
b) administering said antiplatelet agent to said patient if the patient is considered as responsive at step vi), thereby preventing thrombosis in said patient.

15. The method of claim 14, further comprising a step of diagnosing said patient as having a disorder selected from the group consisting of: at risk for atherothrombosis, stable myocardial ischemia, symptomatic myocardial ischemia, asymptomatic myocardial ischemia, an acute coronary syndrome, coronary artery disease that has been treated with one or several coronary stents, symptomatic peripheral artery disease, asymptomatic peripheral artery, abdominal aorta aneurysm, symptomatic atherothrombosis of cerebral arteries and asymptomatic atherothrombosis of cerebral arteries.

16. The method of claim 5, wherein said steps of measuring are carried out by
contacting the blood sample with a binding partner that binds to the GPVI dimer with high affinity; and
detecting platelets bound by said binding partner.

17. The method of claim 6, wherein said steps of determining are carried out by
contacting the blood sample with a binding partner that binds to the GPVI dimer with high affinity; and
detecting platelets bound by said binding partner.

18. The method of claim 6, wherein said activator of platelets is ADP (adenosine diphosphate).

19. The method of claim 14, wherein said activator of platelets is ADP (adenosine diphosphate).

* * * * *